(12) United States Patent
Mizobe

(10) Patent No.: US 6,467,335 B1
(45) Date of Patent: Oct. 22, 2002

(54) DEVICE AND METHOD FOR MEASURING AIR PERMEABILITY

(76) Inventor: Kunitaka Mizobe, 1-6-7, Hoshikuma, Jyonan-ku, Fukuoka-shi, Fukuoka (JP)

( * ) Notice: Subject to any disclaimer, the term of this patent is extended or adjusted under 35 U.S.C. 154(b) by 0 days.

(21) Appl. No.: 09/889,707

(22) PCT Filed: Jul. 26, 1999

(86) PCT No.: PCT/JP99/03997

§ 371 (c)(1),
(2), (4) Date: Jul. 18, 2001

(87) PCT Pub. No.: WO00/42413

PCT Pub. Date: Jul. 20, 2000

(30) Foreign Application Priority Data

Jan. 18, 1999 (JP) ................................. 11-9150

(51) Int. Cl.[7] .......................... G01N 15/08; G01N 5/02; G01M 3/16
(52) U.S. Cl. .......................................... 73/38; 73/29.01
(58) Field of Search .................... 73/38, 29.01, 76, 73/159

(56) References Cited

U.S. PATENT DOCUMENTS

| | | | | | |
|---|---|---|---|---|---|
| 4,766,761 A | * | 8/1988 | Lee | ................. | 73/38 |
| 4,862,730 A | * | 9/1989 | Crosby | ................. | 73/38 |
| 5,535,615 A | * | 7/1996 | Kent et al. | ................. | 73/38 |
| 5,728,930 A | * | 3/1998 | Virta | ................. | 73/38 |
| 5,736,632 A | * | 4/1998 | Nishida et al. | ................. | 73/38 |
| 5,780,720 A | * | 7/1998 | Swain | ................. | 73/38 |
| 5,837,888 A | * | 11/1998 | Mayer et al. | ................. | 73/38 |
| 5,907,091 A | * | 5/1999 | Pause | ................. | 73/38 |
| 6,055,850 A | * | 5/2000 | Turner et al. | ................. | 73/38 |
| 6,196,055 B1 | * | 3/2001 | Haines | ................. | 73/38 |
| 6,294,134 B1 | * | 9/2001 | Schenk et al. | ................. | 422/102 |
| 6,248,711 B1 | * | 10/2001 | Volfkovich et al. | ................. | 73/38 |

OTHER PUBLICATIONS

JIS P8117, "Paper and Board–Determination of Air Permeance–Gurley Method", publication date of 1998, 14 pgs.

* cited by examiner

Primary Examiner—Hezron Williams
Assistant Examiner—David J. Wiggins
(74) Attorney, Agent, or Firm—Flynn, Thiel, Boutell & Tanis, P.C.

(57) ABSTRACT

A technology for measuring an air permeability which can avoid, by using pure water in place of oil as a sealing liquid, adverse effects by oil mist and can accurately measure an air permeability by identifying variations in vapor concentration to be caused by using water. A device for measuring an air permeability installed in a constant temperature/humidity room, wherein an air chamber (22) is formed inside an inner tube (2) with the inner tube fitted in an outer tube (1) storing a sealing liquid, a sample clamping unit (5) that clamps a test sample is provided between an air passage (3) extending from the air chamber through the bottom of the outer tube and an exhaust passage (42) facing the air passage, pure water (W) is used as the sealing liquid, and a temperature/humidity measuring unit (6) and an air supply port (7) opened/closed by a solenoid valve (71) are provided in the vicinity of the sample clamping unit in the air passage.

8 Claims, 4 Drawing Sheets

DEVICE AND METHOD FOR MEASURING AIR PERMEABILITY

FIELD OF THE ART

The present invention relates to a device and method for measuring an air permeability of an air permeable film or other paper or cardboard installed in a device for removing water vapor for dehumidification in a frame.

BACKGROUND ART

The air permeability test method using paper or cardboard specified by JIS P8117 is known as a conventional air permeability measurement method.

In this JIS P8117, an inner tube is fitted in an outer tube storing a sealing liquid so that the inner tube can slide up and down, an air passage extends from an air chamber formed inside the fitted inner tube to the bottom of the outer tube, and a sample clamping unit is provided between the air passage and an exhaust passage. In this method, oil was used as a sealing liquid.

However, when oil is used as a sealing liquid, oil mist is mixed in passing air. Essentially, the air permeability measurement is to measure permeability of air containing water vapor and oil mist is therefore a hindrance for the air permeability measurement. Then this oil mist is mixed in the passing air, the oil mist adheres onto a sample and blocks permeation and, as a result, it is undeniable that an error occurs in a measurement result.

Therefore, use of water as a sealing liquid can be thought for avoidance of an influence by the oil mist.

When water is used as a sealing liquid, water vapor generated by evaporation of the water is spread in passing air within the air chamber or the air passage.

Closer to the water surface, higher the vapor concentration. Therefore, the water vapor gradually flows into the air passage as the inner tube slides down, and humidity starts rising gradually from the start of the measurement. Because such humidity variation can be an error cause in the air permeability measurement, this humidity need be calculated to obtain humidity in the passing air as a requirement for air permeability evaluation.

The present invention is done to solve the above-mentioned problem of the conventional method. The bad influence of the oil mist can be avoided by using pure water in place of oil as a sealing liquid.

The subject is to provide the unit and method for measuring an air permeability that enable precise air permeability measurement by using water and seizing variations in vapor concentration.

In addition, a measurement under an influence of a difference between surface temperatures of a vapor exhaust port and a vapor supply port of a sample being measured and a measurement under an influence of an electrical charge on the sample being measured will be enabled.

DISCLOSURE OF THE INVENTION

To solve the aforementioned problem, the device for measuring an air permeability according to the present invention (claim 1) is:

a device installed in a constant temperature/humidity room wherein;

an inner tube having an opened bottom is fitted in an outer tube having an opened top and storing a sealing liquid so that the inner tube can slide up and down;

an air chamber is formed inside the fitted inner tube; pure water is used as said sealing liquid in the device for measuring an air permeability wherein a sample clamping unit is provided between an air passage extending from the air chamber to the bottom of the outer tube and an exhaust passage facing the air passage; and a device for measuring humidity, a device for measuring a temperature, and an air supply port opened/closed by a solenoid valve are installed in the vicinity of the sample clamping unit in said air passage.

In this case, one embodiment (claim 2) shows that an exhaust fan is installed facing the exhaust passage.

The method for measuring an air permeability according to the present invention (claim 3) is;

a method for measuring an air permeability by using said device for measuring an air permeability comprising;

a primary process of measuring humidity wherein the inner tube is raised to a specific height while air is taken into the air chamber from the air supply port with an impermeable sample set in the sample clamping unit, then the inner tube is freed after the air supply port is closed and, in this state, humidity is measured using the device for measuring humidity;

a secondary process of measuring humidity wherein the inner tube is lifted up to a specific height while air is taken into the air chamber from the air supply port with a sample for measurement set in the sample clamping unit, then the inner tube is freed after the air supply port is closed and, in this state, humidity and a temperature are measured with the lapse of time using the devices for measuring humidity and a temperature; and a process of measuring a drop time carried on simultaneously with the secondary process of measuring humidity wherein a time required for the inner tube to drop for a specific amount is measured and calculating an amount of moisture permeation by subtracting a value obtained from said secondary process of measuring humidity from a value obtained from said primary process of measuring humidity.

In this case, one embodiment (claim 4) shows that an exhaust process wherein exhaust air is exhausted by an exhaust fan from the air chamber through the air passage and the exhaust passage is provided as a preprocess for the primary and secondary processes of measuring humidity.

Embodiments of this method of measuring an air permeability, also include:

an embodiment (claim 5) showing that a perforated plate is provided in the vicinity of a sample to be measured in a vapor exhaust port of the sample, then this perforated plate and the sample are set in the sample clamping unit, and in this state, an air permeability is measured with a difference between temperatures on the surfaces of the vapor exhaust port and vapor supply port or while giving a temperature difference by using a feature that a temperature on the surface of the vapor exhaust port of the sample being measured is changed by heat transfer from the outer tube or other part through the thermal conductivity of the perforated plate;

another embodiment (claim 6) showing that the perforated plate was selected from a multiplicity of perforated plates having different thermal conduction speeds; and another embodiment (claim 7) showing a measurement with the perforated plate grounded or ungrounded.

BEST MODE FOR CARRYING OUT THE INVENTION

Embodiments of the present invention will be explained with reference to drawings.

Figure 1:
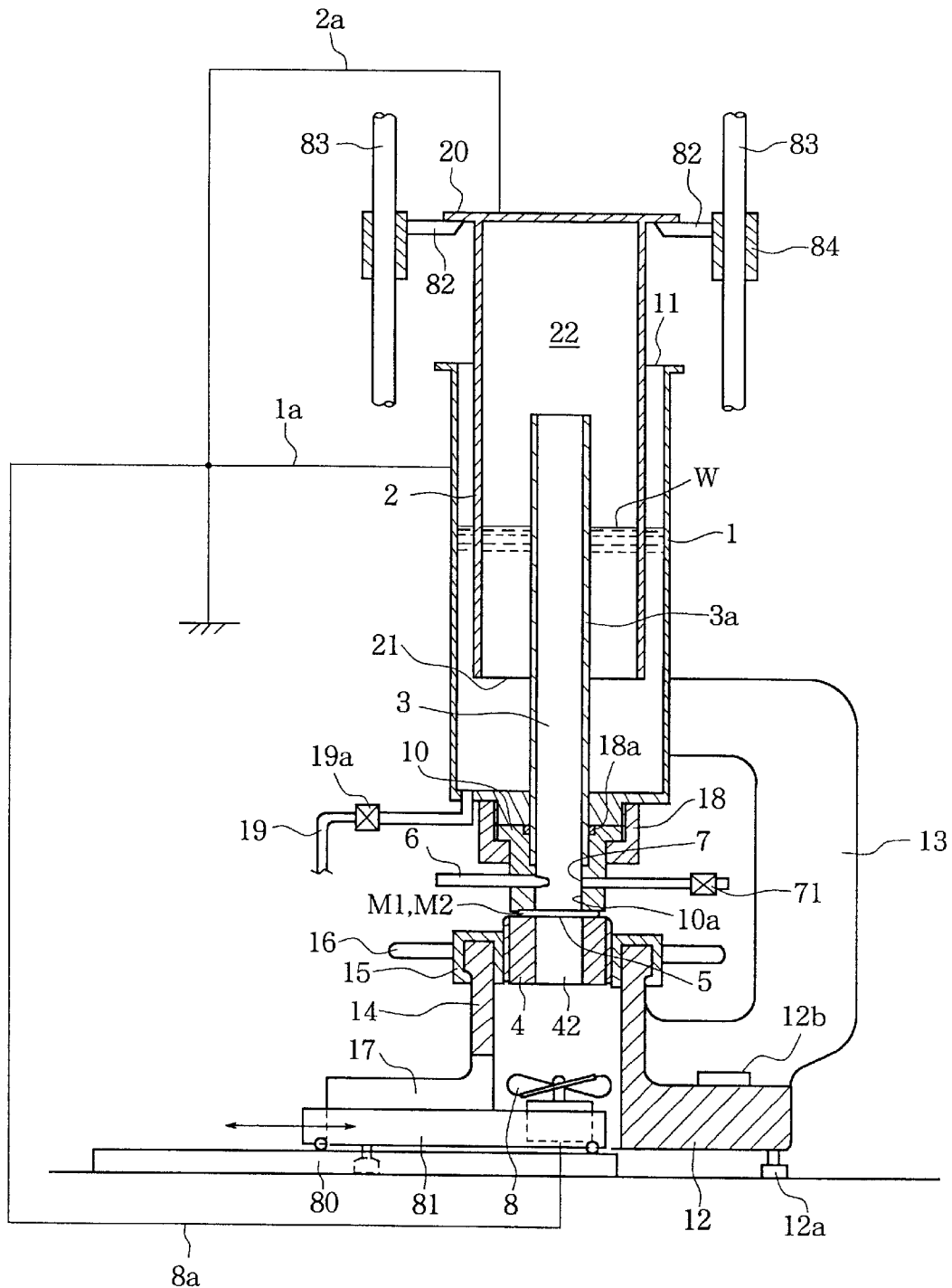
FIG. 1 is a cross-sectional view of an example of the device for measuring an air permeability.
Figure 2:
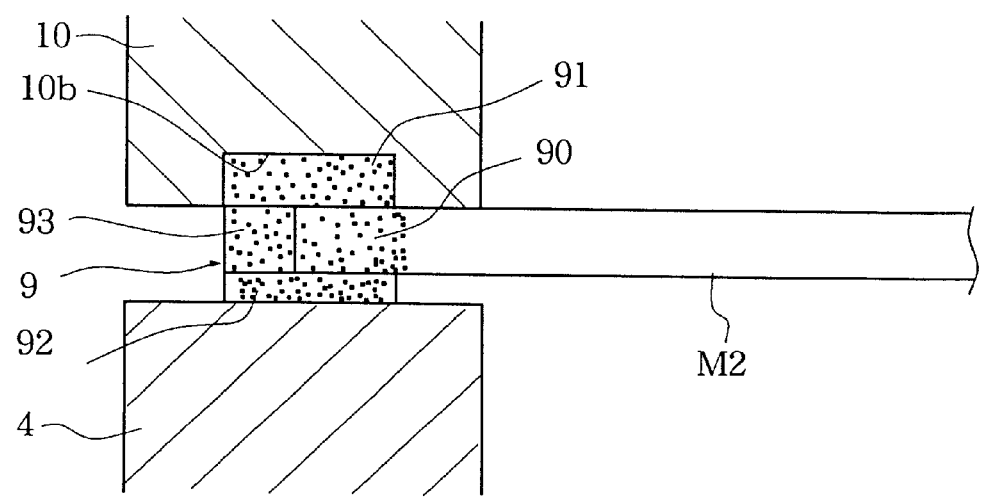
FIG. 2 is an expanded cross-sectional view showing a film seal section.

FIG. 1 is a cross-sectional view of the device for measuring an air permeability according to one embodiment.

This device for measuring an air permeability is equipped with the outer tube 1 having the opened top and storing pure water W used as a sealing liquid and the inner tube 2 having the opened bottom 21 and flange 20 is formed around the circumference of the top.

The outer tube 1 and inner tube 2 are made of a metal having a high thermal conduction speed such as aluminum or stainless steel and passivation, anticorrosion, or corrosion protection processing (alumina processing) is applied on the surfaces of the tubes for corrosion prevention. In addition, numeral 19 in the drawing designates a drain hose having the solenoid valve 19a.

Said outer tube 1 is linked with the base 12 in a unit via linkage frame 13, the inner tube 2 is fitted in the outer tube 1 so that the inner tube 2 can slide up and down, and the air chamber 22 is formed inside the fitted inner tube 2.

Conductors 1a and 2a are provided in the outer tube 1 and the inner tube 2 for electrical concatenated grounding. In this case, a very thin and soft cable should be used for the conductor 2a so that it does not hinder upward and downward sliding of the inner tube.

The conductor 1a and 2a have effects of preventing an electrolytic corrosion through the pure water W used as a sealing liquid in the outer tube 1 and the inner tube 2 and of preventing water vapor in the inner tube 2 from being charged.

A tube 14 is provided on the same axis as the center axis of the outer tube 1 in said base 12, a fastening nut 15 is mounted on the top of this tube 14 so that the nut can be turned, and a elevator 4 is screwed on the fastening nut. Numeral 16 designates the handle of the fastening nut.

Furthermore, a window 17 is formed on the base 12 by notching one side of the tube 14.

Furthermore, a level adjustment screw 12a is movably joined on the bottom of said base 12 to vertically adjust the outer tube 1 and inner tube 2 while watching a level meter 12b.

Then, an air passage 3a extending from said air chamber 22 of the inner tube 2 to the bottom of the outer tube 1 is provided, a clamping unit material 10 is detachably mounted, and an air passage 3 is formed by connecting an inner hole 10a formed in said clamping unit material 10 and the air passage 3a. In addition, numeral 18a designates a squeeze packing.

Furthermore, an exhaust passage 42 facing said air passage 3 is formed in said elevator 4, and a sample clamping unit 5 is provided between said exhaust passage 42 and the air passage 3.

Said sample clamping unit 5 is formed to clamp a metal plate M1 as an impermeable sample or a thin film M2 as a sample to be measured between the bottom of the clamping unit material and the top of the elevator 4.

In addition, a seal 9, is installed on the circumference of the thin film M2 to prevent air leakage. When said seal 9 is formed, the circumference of the film M is impregnated by low viscosity (=40 Pa.s) silicon 90 together with packings 91 and 92 made of silicone rubber formed on the top and bottom of the circumference, and non-fluid silicone 93 is filled between packings 91 and 92 to cover the circumference of the thin film M2. In addition, numeral 10b in the figure designates the seal fitting groove.

Furthermore, on said sample clamping unit material 10, a device for measuring a temperature and humidity 6 having both measurement functions for measuring humidity and temperature and an air supply port 7 opened/closed by a solenoid valve 71 are provided in the air passage 3 in the vicinity of the sample clamping unit 5.

Furthermore, in the tube 14 of said base 12, an exhaust fan 8 is provided facing the exhaust passage 42.

Said exhaust fan 8 is mounted on a movable table 81 set on a rail 80, and can be moved into the tube 14 through said window 17. In addition, a conductor 8a for electrical concatenated grounding is also provided in said exhaust fan 8.

Furthermore, on the side of said inner tube 2, a lift-up unit 84 is provided to lift up and down retainer materials 82, 82 along guides 83, 83.

A means for driving said lift-up unit 84, a manual force, electric motor, air cylinder, or old cylinder can be used, and as means for power transfer, a wire, chain, gear, and link can be used. These means for driving and power transfer are combined to construct a mechanism that retains the retainer material 82 on the bottom of a flange 20 and lift up the retainer material 82, then separate the retainer material 82 from the flange 20 at the elevated position.

Hereinafter, a method of measuring an air permeability by using said device for measuring an air permeability will be explained.

According to this method of measuring an air permeability, the device for measuring an air permeability is installed in a constant temperature/humidity room. The above-mentioned measure is required to prevent an error in a measurement result caused by a change in a temperature or humidity of an atmospheric air because a sample is easily affected by a temperature or humidity.

Operation processes

Operation processes comprise:

a primary process of measuring humidity;

a secondary process of measuring humidity and a process of measuring a drop time; and an exhaust process as a preprocess for the primary and secondary processes for measuring humidity.

Exhaust process

The exhaust fan 8 is moved by the movable table 81 into the tube 14 through the window 17 without the sample M mounted and operate the fan 8 below the exhaust passage 42. By the operation of this exhaust fan 8, air in the air chamber 22 is exhausted or mixed through the air passage 3 and the exhaust passage 42 to make it close to an atmosphere in a constant temperature/humidity room together with drying water drops adhered on the device for measuring a temperature and humidity 6. By the above-mentioned operation, the primary and secondary process of measuring humidity can be carried on under the same conditions. In addition, when a blower fan is used instead of the exhaust fan 8, insides of the air chamber 22 and the air passage 3 and pure water W may be stained by dust sent with air. To prevent the stain, the exhaust fan 8 is used.

Primary process of measuring humidity

After the exhaust process is completed, the fastening nut 15 is turned to elevate the elevator 4 and clamp the metal plate M1 as an air permeability sample in the sample clamping unit 5.

Because said metal plate M1 is impermeable, the air passage 3 is blocked.

The solenoid valve 71 is opened with the metal plate M1 thus set in the sample clamping unit 5 and the inner tube 2 is lifted up to a specific height while the air in the constant temperature/humidity room is taken from the air supply port 7 into the air chamber 22. In this case, the inner tube 2 is gently lifted up at a constant speed by the retainer materials 82, 82 of the lift-up unit 84 being retained on the flange 20.

Hereinafter, the retainer materials 82, 82 of the lift-up unit 84 are separated from the flange 20 after the solenoid valve 71 is closed to close the air supply port 7. By the above-mentioned operation, the inner tube 2 is freed and starts dropping by its own weight. At this time, because the air passage 3 is blocked by the metal plate M1, the inner tube 2 cannot drop and stops in halfway.

In this state, a temperature and humidity are measured using the device for measuring a temperature and humidity 6 with the lapse of time, and this is the primary process of measuring humidity.

Secondary process of measuring humidity and process of measuring a drop time

After the primary process of measuring humidity is completed, the metal plate M1 is removed for said exhaust process, and after this exhaust process is completed, the elevator 4 is raised and the sample clamping unit 5 clamps the thin film M2 as a sample to be measured. By the above-mentioned operation, the air passage 3 and the exhaust passage 42 are connected with the thin film M2 between. At this time, the silicone packing 91 of the thin film M2 fits into the seal fitting groove 10b of the clamping unit material 10. The inner tube 5 is lifted up to a specific height by using the lift-up unit 84 while the air in the constant temperature/humidity room is taken into the air chamber 22 from the air supply port 7 by opening the solenoid valve 71 with the thin film M2 thus set in the sample clamping unit 5.

Hereinafter, the retainer materials 82, 82 of the lift-up unit 84 are separated from the flange 20 after the air supply port 7 is closed by closing the solenoid valve 71. By the above-mentioned operation, the inner tube 2 is freed and starts dropping by its own weight.

In this state, the air in the air chamber 22 is thrust out from the air passage 3 to the exhaust passage 42 through the thin film M2. A temperature and humidity of said thrust-out air is measured by using the device for measuring a temperature and humidity 6 with the lapse of time in the second process of measuring humidity, and at the same time, a time required for the inner tube to drop for a specific amount in the process of measuring a drop time.

Hereinafter, a value of said secondary humidity measurement is subtracted from a value of said primary humidity measurement to obtain an amount of water vapor permeation. By checking said amount of water vapor permeation, a vapor concentration in permeated air can be seized with the lapse of time. By making said amount of vapor permeation and the drop time requirements of evaluating an air permeability, a precise air permeability can be recognized.

Figure 3:
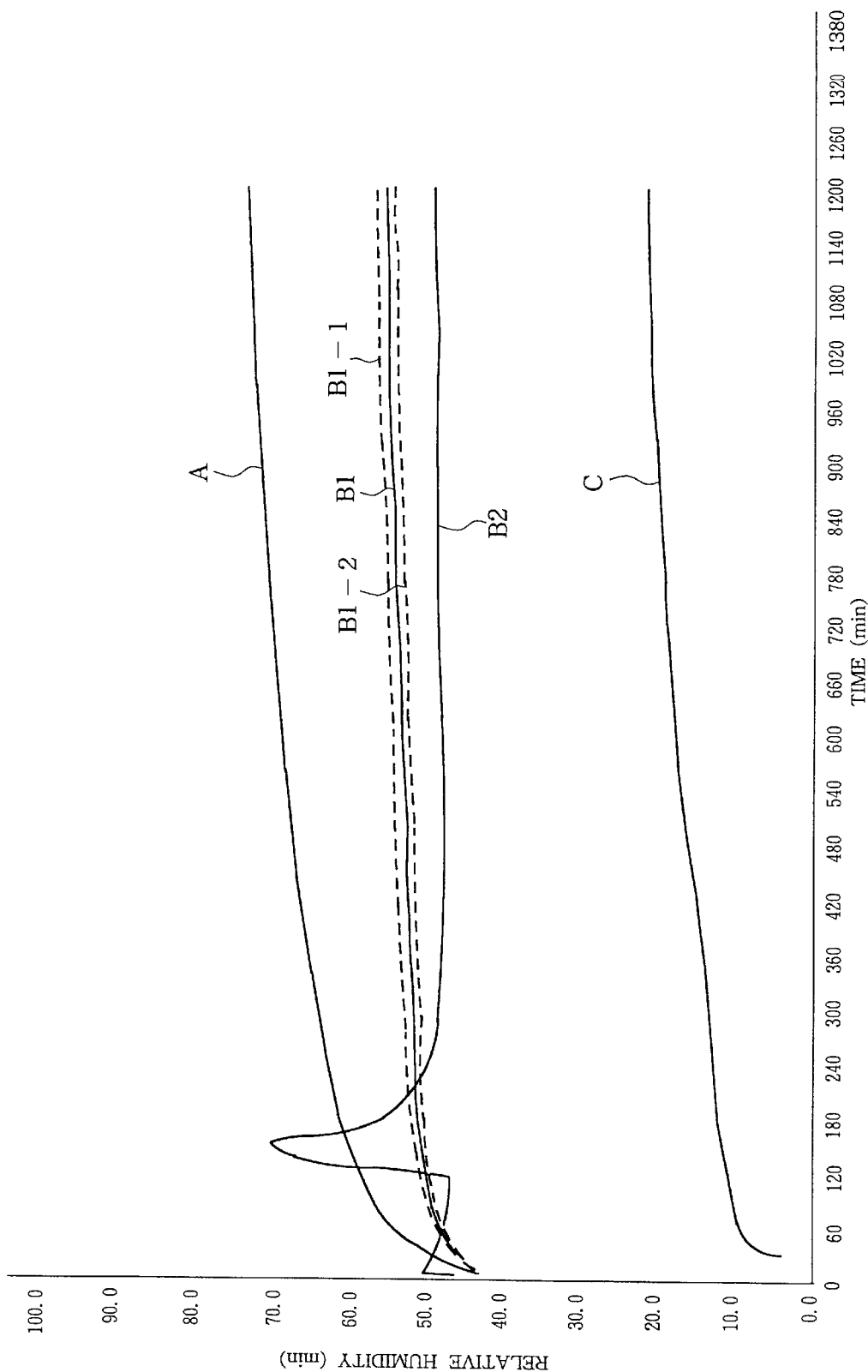
FIG. 3 is a graphical representation showing humidity values measured by the device for measuring humidity.

In addition, FIG. 3 is a graphic representation showing a humidity value measured using the device for measuring humidity 6, a thin film used as a sample made of permeable nonwoven fabric has one side formed to a water repellent surface by water repellent finishing and another side remained to be nonwoven fabric.

In the figure, A designates a value of the primary humidity measurement, B1 designates a value of the secondary humidity measurement when the sample is set with the water repellent side up, B2 designates a value of the secondary humidity measurement when the sample is set with the nonwoven fabric side up, C is an amount of vapor permeation obtained from subtracting the value of the secondary humidity measurement B1 from the value of the primary humidity measurement value A. Said values are measured with the temperature and humidity in the constant temperature/humidity room set to 20° C. and 65% RH. In this figure, an amount of vapor permeation obtained by subtracting the value of the second humidity measurement B2 from the value of the primary humidity measurement A is omitted.

In addition, because the water repellent surface of the thin film sheds water and, on the other hand, the nonwoven fabric side easily absorbs water, there is a difference between the value of the secondary humidity measurement B1 with the water repellent surface up and the value of the secondary humidity measurement B2 with the nonwoven fabric side up. That is, the thin film may actually be used with either the water repelling surface up or the nonwoven fabric surface up and humidity need be measured under either using condition.

Furthermore, when air leaks from a pinhole on the thin film to be measured or a packing, the values B1 and B2 of the secondary humidity measurement shift down in the graphic representation shown in FIG. 3 and air leakage can be detected from these shifted-down values.

Furthermore, because the inner tube 2 is lifted up by the lift-up unit 84 in this measurement method, the inner tube 2 can vertically be lifted up with a measurement space isolated from the atmospheric air.

Therefore, the constant temperature/humidity room can be opened only when the metal plate M1 and thin film M2 are mounted and dismounted and other work can be carried on with the constant temperature/humidity room closed.

By the above-mentioned feature, the atmosphere in the constant temperature/humidity room can be maintained to as a constant temperature and humidity state as possible and error occurrence in a measurement result by an influence of a temperature or humidity of the atmospheric air can be prevented.

Figure 4:
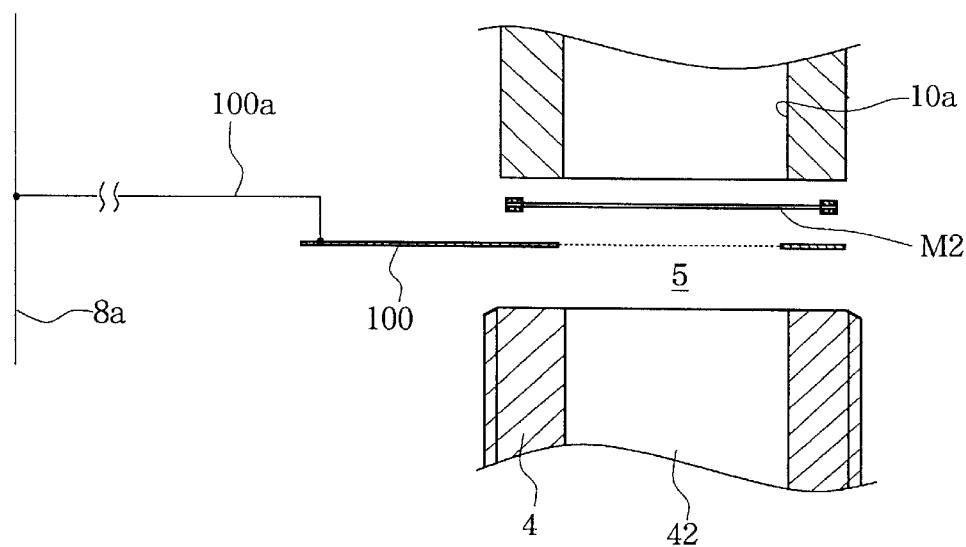
FIG. 4 is a cross-sectional view showing main sections of the device for measuring an air permeability used in another embodiment of the method for measuring an air permeability.

Hereinafter, FIG. 4 is a cross-sectional view showing main sections of the device for measuring air permeability used in another embodiment of the method of measuring an air permeability.

According to this method of measuring an air permeability, the perforated plate 100 installed in the vicinity of the thin film 2 in the vapor exhaust port of thin film M2 used as a sample and the thin film M2 are clamped in the sample clamping unit 5.

Furthermore, said perforation plate 100 was selected from a multiplicity of perforated plates having different thermal conduction speeds such as mesh plates having high thermal conduction speeds made of aluminum, copper, platinum and stainless steel, and a mesh plate having a low thermal conduction speed made of resin. In addition, passivation processing is applied to the surface of the perforated plate for rust prevention.

Furthermore, according to this method for measuring an air permeation, the perforated plate 100 and a conductor 8a are interconnected with a conductor 100a to ground the perforated plate 100.

The thin film M2 to be a sample is used for various purposes and in various places and may be grounded to places with different temperatures separated by the thin film M2 as a boundary. To deal with such use, it is a matter of course that an essential air permeability of the thin film M2 need be measured accurately and also, an air permeability need be measured in a state where a difference between surface temperatures of a vapor supply port and a vapor exhaust port of the thin film M2 is deliberately set.

To accurately measure an essential air permeability of the thin film M2, surface temperatures of the vapor supply port and the vapor exhaust port of the thin film M2 are required to be the same. However, the surface temperature of the vapor supply port of the thin film M2 is affected by heat conduction from the outer tube 1 or other section and, on the other hand, because the surface temperature of the vapor exhaust port of the thin film M2 is affected by a temperature of a measurement space through the exhaust passage 42, there is a difference between surface temperatures on the vapor supply port and vapor exhaust port of the thin film M2.

Therefore, when a perforated plate having a special high thermal conduction speed (e.g., copper mesh plate) is selected and used as the perforated plate 100 as aforementioned, the perforated plate 100 is affected by a temperature of the outer tube 1 or other section by thermal conduction from the outer tube 100 or other section and, as a result, the surface temperatures of the vapor supply port and the vapor exhaust port of the thin film M2 can be made the same.

Therefore, when an air permeability is measured in the above-mentioned state, an essential air permeability of the thin film M2 can be measured accurately. In addition, a standby time necessary for sufficient heat transfer from the outer tube 1 or other section to the perforated plate 100 is prepared for measurement.

On the other hand, to seize an air permeability corresponding to use conditions of the thin film M2 to be a sample, an air permeability need be measured with a difference between the surface temperatures on the vapor supply port and vapor exhaust port deliberately set.

In such case, an air permeability can be seized when there are various temperature differences between the surface temperatures on the vapor supply port and the vapor exhaust port of a specific thin film M2 by preparing several types of perforated plates 100 having different thermal conduction speeds and measuring air permeability by using those perforated plates 100.

In addition, the graphic representation in FIG. 3 shows a value of the secondary humidity measurement in the case of using the copper mesh plate having a special high thermal conduction speed as a perforated plate 100 when the thin film M2 is set with the water repelling surface up. The graph representation in FIG. 3 shows a value of the secondary humidity measurement in the case of using the resin mesh plate having a specially slow thermal conduction speed as a perforated plate as B1-2. In FIG. 3, a value of the secondary humidity measurement in the case of using a perforated plate when the thin film M2 is set with the nonwoven fabric surface up is omitted.

Thus, when the perforated plate 100 is used, measurement with even temperature distribution on the thin film M2 is possible while the surface temperature on the thin film M2 is matched to the temperature on the measurement device by the thermal conductivity of the perforated plate 100.

Furthermore, to seize an influence of variations in a surface temperature on the thin film M2 caused by a heat of vaporization of water drops adhered on the thin film M2 to the value of the second humidity measurement, the blower fan can be used to fan the surface of the thin film M2 at measurement. At this time, in measurement with the perforated plate 100 provided, wind is blocked and has a few influence and, on the other hand, because the surface of the thin film M2 is fanned in measurement without the perforated plate 100, the water drops are easily evaporated by an influence of wind. A degree of variations in an evaporation heat can be seized with air permeation data by collecting data of measurements with and without the perforated plate 100.

Furthermore, because the thermal conductivity and electrical conductivity of the perforated plate 100 are almost proportional, by using this feature, basic data for adjusting movement of water vapor can be obtained with the dielectric relaxation of the thin film M2.

Furthermore, when the perforated plate 100 is charged, the static electricity keeps water drops adhered on the thin film M2 and these water drops hinder accurate measurement of an essential air permeability. Therefore, when perforated plate 100 is grounded, the charge of the thin film M2 is relaxed and the hindrance by adhered water drops is eliminated so that an air permeability can be measured accurately.

Furthermore, when an air permeability of the thin film M2 is measured, an air permeability in a state where the perforated plate 100 is charged need also be seized. In such case, by deliberately removing the grounding of the perforation plate 100, an air permeability can be measured in a state where the perforated plate 100 is changed.

A concrete configuration is not limited to the embodiments of the present invention so-far explained with reference to the drawings.

When perforated plates are used, influences to moisture permeability in the case of combining perforated plates having different thickness features and physical properties can precisely be measured. For example, precise measurement using a perforated plate having the thick center and thin circumference or a perforated plate having a high thermal conduction speed in the center and a low thermal conduction speed in the circumference is possible.

FIELD OF THE INVENTION

As so-far explained, because the present invention uses pure water as a sealing liquid in place of oil, a bad influence by oil mist can be prevented.

Furthermore, variances of vapor concentration can be seized from an amount of a moisture permeability obtained by subtracting a value of the secondary humidity measurement from a value of the primary humidity measurement.

Therefore, by making said amount of a moisture permeability and the drop time requirements for evaluating an air permeability, an effect of recognizing a precise air permeability can be obtained.

Furthermore, when the perforated plate is used for the method of measuring an air permeability according to the present invention, an essential air permeability of a sample can accurately be measured and, in addition, an air permeability can be seized when there are various temperature differences between surface temperatures of the vapor supply port and the vapor exhaust port.

Furthermore, when the perforated plate is grounded, a charge on the sample is relaxed and, as a result, an accurate air permeability can be measured by eliminating the hindrance of water drops adhered on the sample, and also, an air permeability without the perforated plate grounded can be measured if necessary.

I claim:

1. A device for measuring an air permeability installed in a constant temperature/humidity room wherein:

an inner tube having an opened bottom is fitted in an outer tube having an opened top and storing a sealing liquid so that said inner tube can slide up and down;

an air chamber is formed in said fitted inner tube;

a sample clamping unit that clamps a sample between an air passage extending from said air chamber to the bottom of said outer tube and an exhaust passage facing said air passage, and pure water is used as a sealing liquid in said device for measuring an air permeability; and devices for measuring humidity and a temperature in the vicinity of said sample clamping unit in said air passage.

2. The device for measuring an air permeability according to claim 1 wherein an exhaust fan is provided facing said exhaust passage.

3. A method of measuring an air permeability using comprising:

measuring humidity by a primary process including lifting up an inner tube to a specific height while taking air from an air supply port into an air chamber and with an impermeable sample set in a sample clamping unit, then closing said air supply port, then freeing said inner tube and, in this state, measuring humidity with the lapse of time;

measuring humidity by a secondary process including lifting up an inner tube to a specific height while taking air from said air supply port into said air chamber and with a measured sample set in said sample clamping unit, then closing said air supply port, then freeing said inner tube and, in this state, measuring humidity and temperature with the lapse of time; and measuring a drop time by a process including calculating an amount of water vapor permeation by subtracting the value of said secondary process humidity measurement from the value of said primary process humidity measurement.

4. The method for measuring an air permeability according to claim 3 comprising:

an exhaust process including exhausting air from said air chamber by an exhaust fan through an air passage and exhaust passage prior to said primary and secondary processes of measuring humidity.

5. The method for measuring an air permeability according to claim 3 including:

providing a perforated plate in the vicinity of a measured sample on a vapor exhaust port of the sample and, in this state, causing said perforated plate and said sample to face each other in said sample clamping unit; and measuring air permeability with a temperature difference between surface temperatures on said vapor exhaust port and a vapor intake port by varying the temperature on the surface of said vapor exhaust port by the thermal conductivity of the perforated plate.

6. The method for measuring an air permeability according to claim 5 including selecting said perforated plate from a multiplicity of perforated plates having different thermal conduction speeds.

7. The method for measuring an air permeability according to claim 6 including grounding the perforated plate.

8. The method for measuring an air permeability according to claim 5 wherein the temperature difference is substantially zero.

* * * * *